(12) United States Patent
Savic et al.

(10) Patent No.: US 10,426,582 B2
(45) Date of Patent: Oct. 1, 2019

(54) PERFORMED PROSTHESIS-BASE BLANK

(71) Applicant: Kulzer GmbH, Hanau (DE)

(72) Inventors: Novica Savic, Erlensee (DE); Silke Maren Gall, Alzenau (DE); Karl-Heinz Renz, Alzenau (DE); Juliane Stumbaum, Munich (DE); Florian Beuer, Postdam (DE); Josef Schweiger, Bergen (DE)

(73) Assignee: Kulzer GmbH, Hanau (DE)

( * ) Notice: Subject to any disclaimer, the term of this patent is extended or adjusted under 35 U.S.C. 154(b) by 275 days.

(21) Appl. No.: 15/303,288

(22) PCT Filed: Apr. 9, 2015

(86) PCT No.: PCT/EP2015/057710
§ 371 (c)(1),
(2) Date: Oct. 11, 2016

(87) PCT Pub. No.: WO2015/155284
PCT Pub. Date: Oct. 15, 2015

(65) Prior Publication Data
US 2017/0027672 A1 Feb. 2, 2017

(30) Foreign Application Priority Data

Apr. 11, 2014 (DE) .................. 10 2014 105 189

(51) Int. Cl.
*A61C 13/01* (2006.01)
*A61C 13/00* (2006.01)
(Continued)

(52) U.S. Cl.
CPC ...... *A61C 13/0022* (2013.01); *A61C 13/0001* (2013.01); *A61C 13/0004* (2013.01);
(Continued)

(58) Field of Classification Search
CPC ............ A61C 13/0022; A61C 13/0001; A61C 13/0004; A61C 13/0006; A61C 13/01; G16G 20/40; G16H 20/40
See application file for complete search history.

(56) References Cited

U.S. PATENT DOCUMENTS 2,101,431 A 12/1937 Groff
9,295,534 B2 3/2016 Ruppert et al.
(Continued)

FOREIGN PATENT DOCUMENTS

DE 202006006286 U1 8/2007
DE 102009056752 A1 6/2011
(Continued)

OTHER PUBLICATIONS

International Preliminary Report on Patentability in International Application No. PCT/EP2015/057710 dated Oct. 12, 2016, 14 pages.
(Continued)

*Primary Examiner* — John E Uselding
(74) *Attorney, Agent, or Firm* — Marshall, Gerstein & Borun LLP

(57) ABSTRACT

A denture base blank a set comprising at least one denture base blank, and a method for production of a denture base for production of a total or partial denture with a subtractive CAM method, wherein the denture base blank comprises a plastic material or a wax, wherein the denture base blank is pre-formed, and wherein a dental arch or a dental arch section is pre-formed as a material thickening of the denture base blank.

27 Claims, 4 Drawing Sheets

(51) Int. Cl.
*G16H 20/40* (2018.01)
*A61C 13/107* (2006.01)

(52) U.S. Cl.
CPC .......... *A61C 13/0006* (2013.01); *A61C 13/01* (2013.01); *G16H 20/40* (2018.01)

(56) References Cited

U.S. PATENT DOCUMENTS

| | | |
|---|---|---|
| 2011/0045442 A1 | 2/2011 | Adusimilli et al. |
| 2012/0258430 A1 | 10/2012 | Ruppert et al. |
| 2013/0326878 A1 | 12/2013 | Boehm et al. |
| 2014/0317930 A1 | 10/2014 | Klingenburg et al. |
| 2016/0193019 A1 | 7/2016 | Heinz et al. |

FOREIGN PATENT DOCUMENTS

| | | | |
|---|---|---|---|
| DE | 102011118320 A1 | 5/2013 | |
| DE | 202013005457 U1 | 6/2013 | |
| DE | 102012201744 A1 | 8/2013 | |
| DE | 102012011371 A1 | 12/2013 | |
| EP | 2742907 A1 | 6/2014 | |
| FR | 2582932 A1 | 12/1986 | |
| JP | 58-5413 | 1/1983 | |
| JP | 6304188 | 11/1994 | |
| JP | 2011524755 A | 9/2011 | |
| WO | WO-91/07141 A1 | 5/1991 | |
| WO | WO-2013/068124 A2 | 5/2013 | |
| WO | WO-2013068124 A2 * | 5/2013 | ......... A61C 13/0004 |
| WO | WO-2013/124452 A1 | 8/2013 | |

OTHER PUBLICATIONS

Office Action in CA Application No. 2,943,018 dated Aug. 31, 2018, 4 pages.
Search Report in International Application No. PCT/EP2015/057710 dated Jun. 19, 2015, 4 pages.
Office Action in EP Application No. 15715254.7 dated Oct. 17, 2018, 17 pages.
Office Action in JP Application No. 2017-504264 dated Aug. 1, 2017, 7 pages.
Office Action in JP Application No. 2017-504264 dated Apr. 4, 2018, 8 pages.
Translation of Rejection Decision in Japanese Application No. 2017-504264 dated Nov. 21, 2018, 2018, 6 pages.

* cited by examiner

PERFORMED PROSTHESIS-BASE BLANK

BACKGROUND OF THE INVENTION

Field of the Invention

The invention relates to a denture base blank for producing a denture base for a dental prosthesis with a subtractive CAM method, wherein the denture base blank consists of a plastic or wax material.

The invention also relates to a method for producing a denture base for a dental prosthesis and a set for implementation with such a denture base blank.

Description of Related Art

The invention thus ultimately relates to the production of partial plastic dentures (partial dentures) and total plastic dentures (total dentures) for dental medicine of denture bases for this purpose which are produced by machine using the CAM method (CAM—Computer-Aided Manufacturing). Preferably, the dental prostheses and denture bases are constructed with the support of a computer using the CAD method (CAD—Computer-Aided Design). Here, initially a denture base is produced which later lies on the toothless or partially toothless gum of a patient. The prosthetic teeth are then finished individually and inserted into the denture base, where they are affixed. The denture base with the arranged prosthetic teeth then forms the finished dental prosthesis.

The standard method is the analog creation of dental prostheses. In order to produce the denture base, an analog method is therefore currently used in which first an imprint of the toothless jaw of the patient is taken. From this imprint, a form is created into which a gum-colored plastic material is poured. After the plastic has hardened, it is post-processed in order to obtain the desired form. The separately produced prosthetic teeth are then inserted, which are currently also produced using an analog method in most cases.

In order to produce the prosthetic teeth, said teeth are manually and individually set up on a wax base. In the next step, this wax prosthesis is embedded in dental plaster in a cuvette, and the wax base is washed out with hot water after the dental plaster has cured to create a hollow space for the denture resin. The prosthetic teeth remain in the dental plaster during this step. A respective dental plaster is injected or "plugged" into the hollow space to result in the denture or the finished prosthetic tooth after the plastic material has cured.

If necessary, when setting up prefabricated prosthetic teeth, the dental technician adjusts them to the patient's oral situation and grinds them.

A method of this type is known from WO 91/07141 A1, in which a denture base is ground on the basis of an imprint from a plastic block. There are already the first methods available, such as that disclosed in DE 10 2009 056 752 A1 or WO 2013 124 452 A1, in which the partial or total denture is digitally set up and is produced via CAD-CAM methods. FR 2 582 932 A1 recommends that a denture base be generated with the aid of a wax imprint and 3D coping mill, but this method is costlier than the modern CAD-CAM methods. A milling block with pre-formed prosthetic teeth is known from WO 2013 068 124 A2. The disadvantage of this is that the prosthetic teeth consist of the same material as the base, and when damaged, the entire set of teeth needs to be replaced and the finished constructed denture can only be adapted to the needs of the patient (for example with regard to the color of the tooth or the occlusion and position of the tooth) at a great cost. A further disadvantage is that the base and the prosthetic tooth (or the prosthetic tooth crown) have different requirements, but are produced from the same material. Thus, the tooth should primarily chew and remain undamaged while doing so. By contrast, the base should distribute the forces that arise over the mucous membrane. This can lead to problems when only one material is used.

A round blank for producing a denture is known from DE 20 2006 006 286 U1. This blank (the so-called round blank) is tensioned in a CAM milling machine and milled automatically on the basis of a CAD model. Current methods mill a denture base from such a full block (the round blank) with a thickness of just 2 mm to 3 mm. Disadvantages are on the one hand a very high use of material, which depending on the anatomical situation of the respective patient can easily amount to over 90%. On the other, this leads to a time-intensive processing time by the CAM device, since a very large amount of material must be removed. Furthermore, the degree of wear of the respective milling tools is relatively high.

A further disadvantage here is that it takes a relatively long time until the denture base has been produced. Additionally, the milling head is subjected to wear during the processing of the blank and must be renewed at regular intervals. The milled off material (the millings) must be disposed of or recycled.

SUMMARY OF THE INVENTION

The object of the invention is thus to overcome the disadvantages of the prior art. In particular, a denture base blank, a method and a set are to be provided with which the simplest, most complete and most cost-effective processing possible of the denture base blank or the simplest, most complete and most cost-effective production of the denture base possible are enabled. The milling head of the tool for implementing the subtractive CAM method should here be subjected to as little wear as possible. Additionally, it should be possible to complete the production of the denture base as quickly as possible.

The objects of the invention are attained by means of a denture base blank for producing a denture base for a dental prosthesis with a subtractive CAM method, wherein the denture base blank consists of a plastic material or a wax in which the denture base blank is pre-formed, wherein a dental arch or a dental arch section is pre-formed in order to thicken the material of the denture base blank.

The fact that the denture arch or denture arch section is pre-formed means that the material for the denture arch to be produced of the denture base or the denture arch section to be produced of the partial denture base is already contained in the material thickening. For this purpose, the dimensions of the denture arch or denture arch section are larger than a group of typical denture arches of denture bases to be produced, including the usual tolerances. Preferably, with a denture base blank according to the invention, between 5% and 100% of all denture bases that can realistically be anticipated can be produced.

The dental arch comprises the form of the denture base, but not of the prosthetic teeth to be inserted. After the prosthetic teeth have been inserted, the set of teeth generated with the denture base blank can therefore be higher than the thickening of the dental arch of the unprocessed denture base blank.

With the invention, it is also recommended that the position and orientation of the denture base to be produced is pre-specified in the denture base blank by the outer form of the denture base blank.

Naturally, a certain degree of freedom remains in order to be able to produce different denture bases from the denture base blank. It is sufficient when the position of the denture base to be produced has an accuracy of 10 mm in the denture base blank, preferably an accuracy of 5 mm, and the orientation of the denture base to be produced in the denture base blank has an accuracy of 10°, preferably of 5°. The orientation here relates to potential tipping angles of the denture base to be produced relative to the pre-formed denture base blank.

It can be provided according to the invention that the denture base blank comprises precisely one symmetry plane or two symmetry planes which are oriented vertically to each other, wherein precisely one symmetry plane is preferred. Preferably, it can here be provided that the one symmetry plane or one of the symmetry planes corresponds to the sagittal plane of the denture base to be produced.

With a further development of the present invention, it is recommended that the dental arch or dental arch section is formed in the occlusal direction away from the contact surface on the gum with a decreasing width.

As a result, the form of the denture base blank is further adapted to the form of normal or standard denture bases which also comprise in the occlusal direction decreasing profiles vertical to the progression of the dental arch. As a result, the quantity of material to be removed or to be milled off during production is further reduced.

According to the invention, it can further be provided that the denture base blank comprises on the side to come into contact with the gum an arched recess as a pre-formation of a retainer of a toothless jaw ridge or a part of a toothless jaw ridge, wherein the recess extends along the dental arch or dental arch section.

This measure also serves to further adapt the form of the denture base blank to the form the denture base to be produced from it, in order to save material and thus time during manufacture and to reduce the degree of wear of the milling tool.

It is also recommended with the present invention that on at least one side of the denture base blank, preferably on a buccal side of the denture base blank, a holder is arranged for fastening the denture base blank to a CAM device, in particular a CAM milling machine, and/or a mark is provided for the positioning of a CAM milling machine.

As a result, it can be ensured that the denture base blank can be tensioned into the CAM device in the correct orientation and the correct position.

According to a preferred embodiment of the invention, it is also recommended that the denture base blank comprises solely rounded corners and edges, preferably with no corner or edge of the denture base blank with a curvature radius of less than 0.5 mm, particularly preferred of less than 2 mm. With embodiments of the denture base blank with a holder for affixing the denture base blank to the CAM device, in particular the CAM milling machine, it can be provided that the denture base blank comprises rounded corners and edges, excluding the holder, preferably with no corner or edge of the denture base blank, excluding the holder, with a curvature radius of less than 0.5 mm, particularly preferred of less than 2 mm.

As a result, it can be prevented that corners and edges of the denture base blank or parts of them break off during processing using the CAM method. Since the holder for the CAM device is not processed and is later only separated, narrower curvature radii and edges can also be realized there.

Further, it can be provided that the denture base blank consists of polymethyl methacrylate (PMMA), polyether ketone (PEK), polyether ether ketone (PEEK), polyamide (PA), polycarbonate (PC) or polyurethane (PU).

These materials are particularly well suited to the processing of the denture base blank with the CAM method. Additionally, aesthetically matching denture bases can also be produced from them.

It can also be provided according to the invention that inorganic filling substances are contained in the material from which the denture base blank is constructed. Preferably, the denture base blank is constructed of a plastic material.

Feasible inorganic filling substances are silicon oxide, ceramics, glass ceramics or their mixtures, and inorganic fibers made of glass, carbon or organic fibers made of polyethylene with an ultra-high molecular weight (UHMW-PE). The filling substances can be distributed in the plastic material in powder form. Preferably, the plastic material can comprise a transparency which gives the denture base a natural appearance.

According to a further embodiment of the present invention, it can be provided that in the interior of the dental arch or dental arch section of the denture base blank and along the dental arch or dental arch section, a stiffening and/or a reinforcement of the material of the denture base blank is or are provided.

As a result, an improvement in the mechanical properties of the denture base produced from the denture base blank can be achieved. The mechanical durability of a dental prosthesis produced in this manner is improved compared to dental prostheses produced in the standard manner using the CAD/CAM method.

According to a particularly preferred further development of the present invention, it can be provided that the dental arch is designed as a parabolic thickening of the material on the edge side of the denture base blank, or the dental arch section is designed as a thickening of the material on the edge in the form of a partial piece of a parabolic form of the denture base blank.

This form offers the best possible initial form for producing different denture bases. The essential formation must namely be conducted in the area of this dental arch. At the same time, through this structure, the form of a denture base is already roughly pre-specified, so that the loss of material during removal can be further minimized.

With such denture base blanks, it can be provided that the thickening has a width of between 8 mm and 30 mm and/or the thickening has a thickness or height between 5 mm and 30 mm. The width and thickness or height of the thickening then corresponds to the width and thickness or height of the dental arch of the denture base blank.

As a result, there is sufficient space for inserting the prosthetic teeth in the thickening of the denture base blank when it is processed using the CAM method.

Further, with these denture base blanks it can be provided that the thickening has a greater thickness or height in the area around the apex of the parabolic thickening than in the arms of the parabolic thickening and/or that the thickness or height of the thickening increases in the direction of the apex of the parabolic section.

As a result, a further adaptation of the form of the denture base blank to the denture base to be produced can be achieved and thus also savings in material.

The objects that form the basis of the present invention are also attained by means of a method for producing a denture base for the production of a total denture or at least a partial denture with a denture base blank, comprising the following method steps:

1) Attachment of the denture base blank in a CAM device for removing material of the denture base blank by means of a CAM method, and 2) removal of material of the denture base blank with the CAM method on the basis of a calculated CAD model.

From the denture base blank according to the invention, either a total denture can be milled or formed for part of a jaw, or several partial dentures can be milled or formed from a denture base blank.

With the method according to the invention, it is also recommended that the denture base blank is selected from a plurality of denture base blanks, wherein the selection is made in terms of calculation on the basis of the CAD model of the denture base to be produced and the known dimensions of all denture base blanks, wherein preferably, by means of an output facility of a computer, all denture base blanks from the selection are recommended and/or can be selected via an input facility.

As a result, a larger number of different denture base blanks can be provided, wherein each denture base blank is already better adapted to the geometry of the denture base to be produced than if only one denture base blank or a small number of denture base blanks were to be available for selection.

Further, according to the invention, it can also be provided that the denture base blank is selected or the denture base blanks are selected from the quantity of denture base blanks the outer dimensions of which can fully hold the form of the denture base to be produced, which is calculated by the CAD model, wherein preferably, the recommended sequence, in particular the displayed or shown sequence, of the selected denture base blanks is determined by the volume difference between the outer form of the denture base blanks and the CAD model of the denture base to be produced.

According to the invention, it can also be provided that the denture base blank is automatically recommended or used which comprises the lowest volume difference to the CAD model of the denture base to be produced.

As a result of these measures, it is possible with a given selection of different denture base blanks to select that or those which can be processed most quickly, or from which the least material needs to be removed.

It is also recommended that when calculating the CAD model of the denture base to be produced, data previously recorded relating to the oral cavity situation of the patient and/or the outer form of the denture base blanks or the outer form of the denture base blank is taken into account.

As a result, a further automation of the method according to the invention is made possible.

Further, it can be provided that with the CAM method in the pre-formed dental arch of the denture base blank, several recesses for holding prosthetic teeth are created, preferably milled, in the denture base produced.

Due to the production of the denture base and the recesses in a single step, time can be saved on the one hand, while on the other, errors can be avoided which can occur with a renewed or separate tensioning and positioning of the half-finished denture base into the same or a different CAM device.

The objects of the present invention are also attained by means of a set comprising at least one denture base blank, preferably a plurality of differently formed denture base blanks, and data regarding the outer form of the at least one denture base blank, preferably comprising a data carrier on which the data is stored.

Here it can be provided that the set comprises several differently formed denture base blanks and data regarding the outer form of all these denture base blanks, and that the set for implementing a method according to the invention is provided.

The invention is based on the surprising finding that with the pre-formed denture base blanks, it is possible to enable a faster and more efficient method for producing denture bases, in which the tools of the CAM device are protected and the material loss from the subtractive CAM method can be minimized. Due to the suitable form, the denture base blanks remain sufficiently flexible during the process in order to be adapted unhindered to the different oral cavity situations and other requirements to which the denture base to be produced is subject.

The denture base blanks, the method and the set are provided for processing with CAD/CAM methods and are particularly suited to these.

The solution approach that forms the basis of this invention is preferably based on various pre-formed denture base blanks which eliminate the disadvantages described above by means of the fact that they are not full body but pre-formed blanks. The invention further stands out for the fact that—similar to impression trays—it divides the human jaw on the basis of anatomical features into categories or sizes and accordingly provides largely pre-formed denture base blanks. The software used in a CAD CAM system then selects the matching denture base blanks for the respective patient situation and adopts the so-called nesting in the pre-formed denture base blanks (the base possible positioning of the virtual form of the denture base to be produced in the denture base blank). The denture base blanks can preferably be produced from different material such as plastics or wax.

The advantages of the denture base blanks according to the invention or the method according to the invention and the set according to the invention lie among other things in the lower milling times, lesser use of material with regard to the denture base material and a protection of the milling tools, i.e. in a lower degree of wear of the milling tools compared to the application of standard milling blanks.

BRIEF DESCRIPTION OF THE DRAWINGS

Exemplary embodiments of the invention will be explained below with reference to four schematic figures, although without restricting the invention, wherein.

In the figures, the same reference numerals are also used in some cases for different embodiments for similar parts.

DETAILED DESCRIPTION

Figure 1:
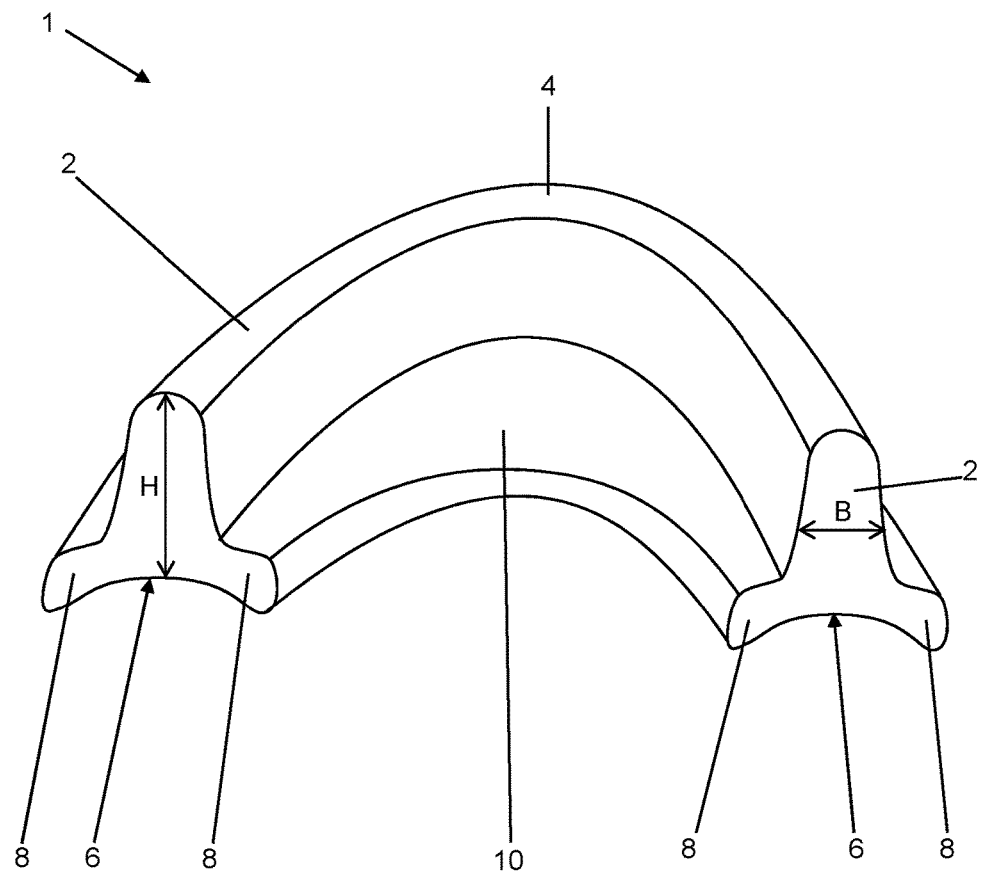
FIG. 1: shows a schematic perspective view of a denture base blank according to the invention.

FIG. 1 shows a schematic perspective view of a denture base blank 1 according to the invention. The denture base blank 1 consists of a plastic material, preferably a polymer. On the edge, the denture base blank 1 comprises a parabolic thickening which forms a pre-formed dental arch 2. The denture base blank 1 is symmetrically oriented to a central plane. This central plane corresponds to the sagittal plane of the patient, into whom the denture produced using the denture base blank 1 is inserted. In the geometric center, i.e. on the sagittal plane, the apex 4 of the parabolic dental arch 2 is located. The apex 4 of the denture base produced from it is later arranged labially, i.e. on the lip side, of the patient, when a total denture is produced from the denture base blank 1, or a partial denture which comprises at least the central incisor teeth.

On the side with which the denture bases to be produced from the denture base blank 1 is placed onto the gum (shown in FIG. 1 below) a recess 6 is provided. The recess 6 is a pre-formation of the contact recess of the denture base to be produced, which is designed to hold the toothless gum of the patient.

At the side adjacent to the dental arch 2, protrusions 8 are provided from which the connection surfaces of the denture base on the jaw side are formed. This protrusion 8 widens orally in the area of the apex 4 to form a central piece 10, from which a contact surface can be formed which is palatinal, i.e. gum-sided, or which lies in contact below the tongue in the oral cavity of the lower jaw.

The dental arch 2 comprises a width B and a height H wherein the width B and the height H can change along the dental arch. With the denture base blank 1 shown in FIG. 1, the height H of the dental arch increases towards the apex 4. In this area, after the denture base has been developed, the incisor teeth or the prostheses of the incisor teeth must be inserted and affixed. The width B of the dental arch 4 is selected to be sufficiently wide that adequate variation of the formation of the denture base to be produced is possible.

The denture base blank 1 shown is suitable both for producing a single partial denture base or several partial denture bases, or a total denture base for a lower jaw and for an upper jaw. However, it is also possible to provide more strongly pre-formed denture base blanks 1, in which a differentiation is made between the upper jaw and the lower jaw. Additionally or alternatively, a plurality of different denture base blanks 1 can be made available or provided as a set, which differ by means of the curve of the dental arch 2 and its width, and from which the matching denture base blank 1 can be selected. The denture base blanks 1 can also differ through different heights H and widths B of the dental arches 2.

Figure 2:
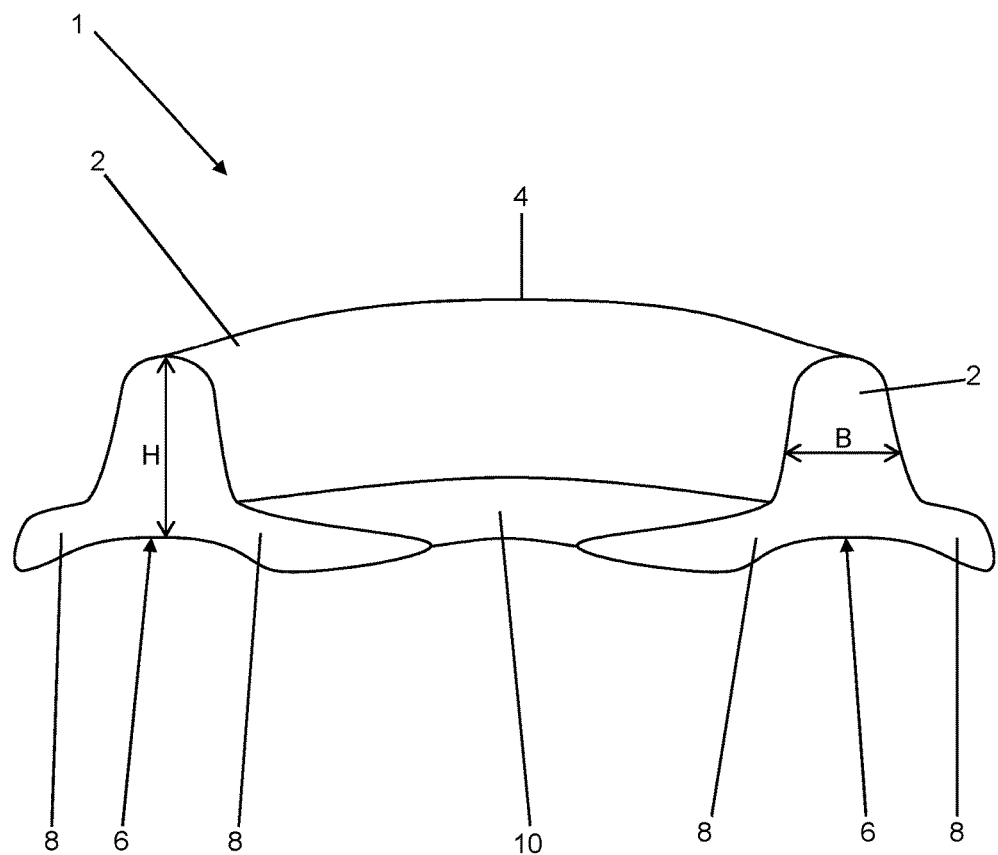
FIG. 2: shows a schematic side view of a denture base blank according to the invention.

FIG. 2 shows a schematic side view of a denture base blank 1 according to the invention. The denture base blank 1 comprises, in a similar manner to that shown in FIG. 1, a dental arch 2 which compared to that shown in FIG. 1, however, comprises a somewhat wider width B. The dental arch 2 extends on the edge in a parabolic form along the denture base blank 1. The height H of the dental arch 2 is enlarged in the area of the apex 4 of the denture base blank 1.

On the lower side of the denture base blank 1, a recess 6 is provided (shown in FIG. 2 below) which serves as a pre-formation of a contact surface of the toothless gum of the patient in the denture base to be produced. At the side adjacent to the thickening 2 through the dental arch 2, widenings 8 or protrusions 8 are provided from which a connection surface to the jaw ridge of the patient can be formed.

The center piece 10 extends with this embodiment of the denture base blank 1 almost to the center, so that from this denture base blank 1 a large-area gum cover can also be formed.

Figure 3:
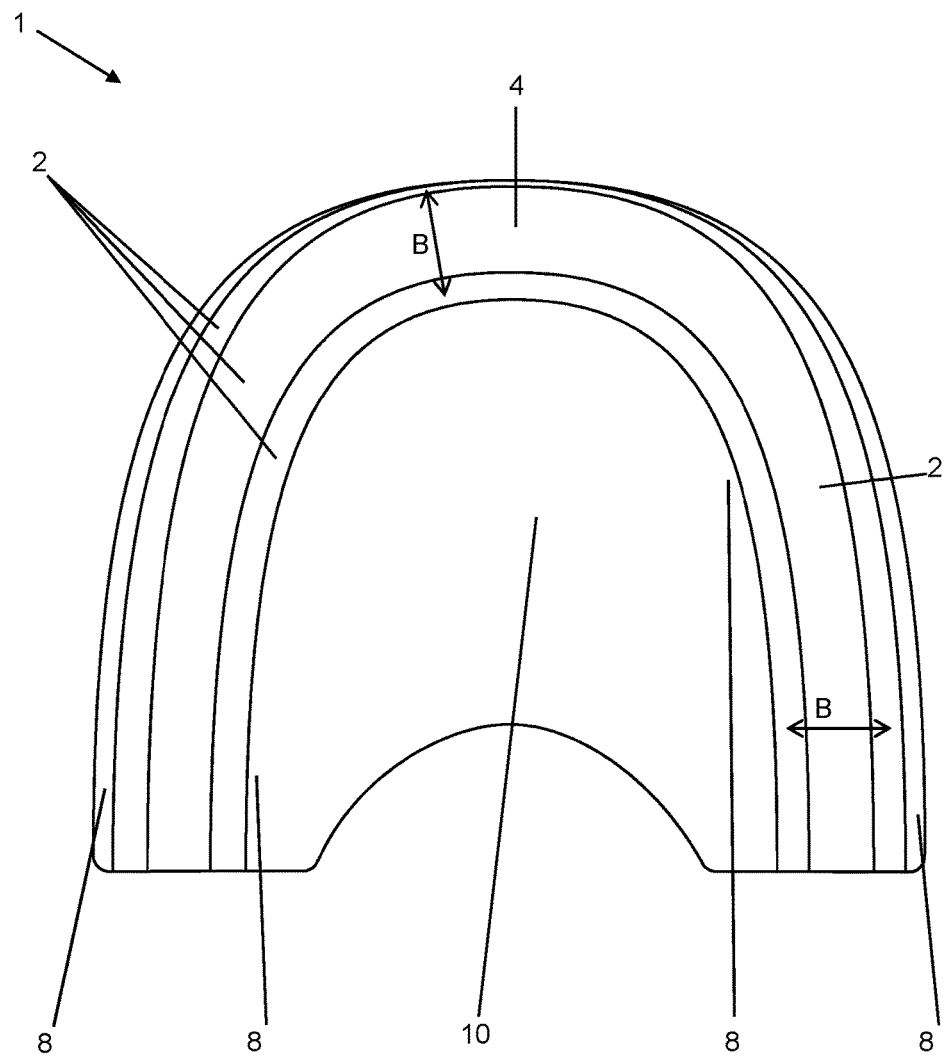
FIG. 3: shows a schematic top view onto a denture base blank according to the invention.

FIG. 3 shows a schematic top view onto a further denture base blank 1 according to the invention. The denture base blank 1 comprises rounded corners in order to prevent the risk of parts of the denture base blank 1 breaking off during processing.

The denture base blank 1 comprises a parabolic thickening on the edge in the form of a dental arch 2 which in a similar manner to the embodiments shown in FIGS. 1 and 2 extends upwards (in FIG. 3 in the direction of the observer). In the area of the apex 4 of the dental arch 2, the height of the dental arch 2 can be greater than on the opposite sides. With the embodiment according to FIG. 3, the width B is also increased in the area of the apex 4.

Adjacent to the dental arch 2, protrusions 8 are provided which serve the same purpose as the protrusions 8 shown in FIGS. 1 and 2. In the center of the denture base blank 1, a center piece 10 is provided from which a gum plate or sublingual support of the denture base to be produced can be created. In the area of the apex 4 of the denture base blank 1, the labial protrusion 8 is strongly reduced or no longer present. The profile of the dental arch 2 also changes along the dental arch 2 vertical to the parabolic curve or vertical to the dental arch 2. The pitch of the labial flank of the dental arch 2 is reduced in the area of the apex 4.

The denture base blanks 1 as shown in FIGS. 1, 2 and 3 are all symmetrically structured with regard to the sagittal plane in which the apex 4 is located. Any possible anatomically necessary asymmetries can be created while milling out the denture base blank 1 during production of the denture base.

In order to produce a denture base, a denture base blank 1 is selected from a plurality of denture base blanks 1 of different sizes and forms. The outer dimensions of the different denture base blanks 1 are stored electronically in a database for this purpose. The oral cavity situation of the patient to be treated is scanned in with the aid of a 3D scanner and digitalized. On the basis of this and if necessary of additional data, a virtual model of the denture base to be produced is generated with the aid of a CAD method.

A test is then conducted as to the denture base blanks 1, singular or plural, into which the denture base to be produced might fit. A list of the possible denture base blanks 1 is offered on a screen of a computer. The sequence can be oriented according to the volume difference between the denture base to be produced and the denture base blank 1, wherein lower volume differences are favored. Alternatively, only the denture base blank 1 can be shown with the lowest volume difference, or only the existing or pre-stored denture base blanks 1. The lower volume difference has the advantage that with these denture base blanks 1, less material needs to be removed than with denture base blanks 1 with a higher volume difference in relation to the denture base to be produced.

A denture base blank 1 is then selected by the user or by the computer and a denture base blank 1 of this type is tensioned into a CAM device such as a CAM four-axle mill. Here, attention must be paid to the correct orientation of the denture base blank 1 in the CAM device. For this purpose, marks or shapes can be provided on the denture base blank 1 which enable, or preferably enforce, a specific position and orientation of the denture base blank 1 in the CAM device.

Then, on the basis of the CAD model of the denture base to be produced, this is milled out of the tensioned denture base blank 1 or produced using another subtractive CAM method.

In this denture base, recesses for holding prosthetic teeth can also be created at the same time. The prosthetic teeth are then glued into the denture base and the denture is complete.

Figure 4:
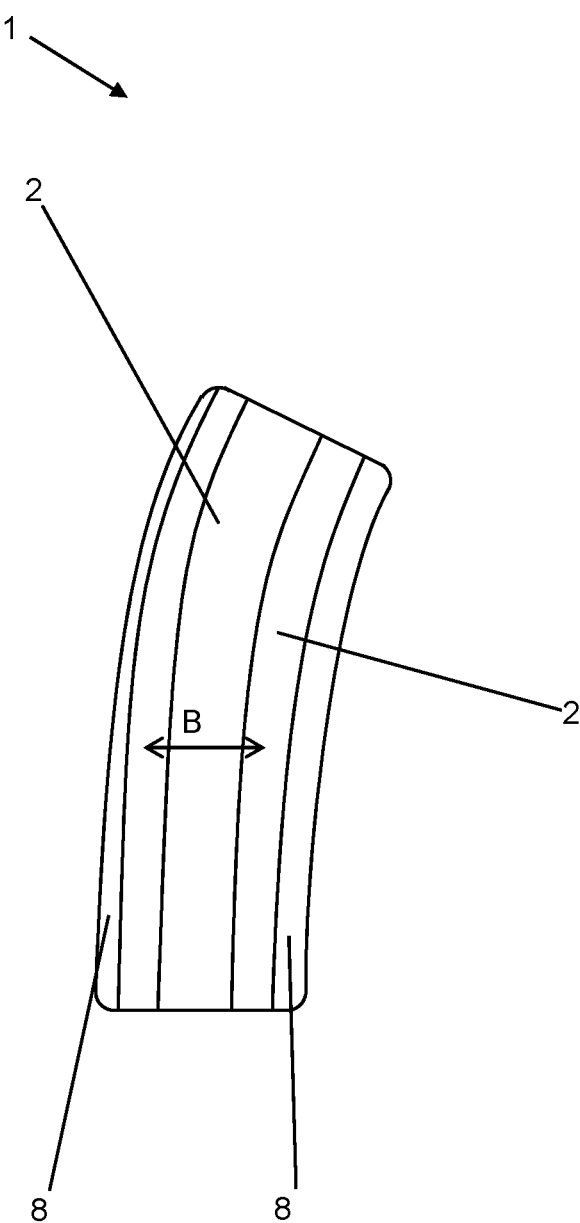
FIG. 4: shows a schematic top view onto a denture base blank according to the invention for a partial denture base.

FIG. 4 shows a schematic top view onto a denture base blank 21 according to the invention for a partial denture base. The denture base blank 21 is in principle a part of the denture base blank 1 shown in FIG. 3 on the jaw side. A dental arch section 22 is provided in the form of a parabolic section as a thickening of the material of the denture base blank 21. Since the width B of the denture base blank 21 is almost as wide as the entire profile of the denture base blank 21, the dental arch 22 is also arranged on the edge in the sense of the present invention with this embodiment. Adjacent to the dental arch 22, short protrusions 28 are provided which fulfill the same purpose as the protrusions 8 of the exemplary embodiments shown in FIGS. 1 and 2.

A recess is provided on the underside of the denture base blank 21 (not shown in the top view shown in FIG. 4), which extends below the upper plateau of the dental arch 22 in the same direction and position. The recess serves as a pre-formation of the later contact surface on the gum of a denture base produced from the denture base blank 21 or the partial denture base created from it.

The manufacturing method for the denture base blank 21 as shown in FIG. 4 runs analog to the method shown in FIGS. 1 to 3, wherein only one partial denture is produced.

The features of the invention disclosed in the above description, and in the claims, figures and exemplary embodiments, can be essential both individually and in any desired combination for the realization of the invention in its different embodiments.

LIST OF REFERENCE NUMERALS 1, 21 Denture base blank
2 Pre-formed dental arch
4 Apex of the dental arch
6 Recess on the contact surface to the gum
8, 28 Protrusion
10 Center piece
22 Pre-formed dental arch section
B Width of the dental arch
H Height of the dental arch

The invention claimed is:

1. A denture base blank for producing a denture base for a denture with a subtractive CAM method, wherein the denture base blank comprises a wax or a plastic material selected from the group consisting of polymethyl methacrylates, polyether ketones, polyether ether ketones, polyamides, polycarbonates, and polyurethanes, the denture base blank is pre-formed, and a dental arch or a dental arch section is pre-formed as a material thickening of the denture base blank, wherein the material for the dental arch or dental arch section to be produced is contained in the material thickening and wherein the dental arch comprises the form of the denture base but not of prosthetic teeth to be inserted in the denture base.

2. The denture base blank according to claim 1, wherein a position and an orientation of the denture base to be produced in the denture base blank is pre-specified by an outer form of the denture base blank.

3. The denture base blank according to claim 1, wherein the dental arch or dental arch section is formed in an occlusal direction away from a contact surface on a gum with a decreasing width.

4. The denture base blank according to claim 1, wherein the denture base blank comprises on a side to come into contact on a gum a curved recess as a pre-formation of a retainer of a toothless jaw ridge or a part of a toothless jaw ridge, wherein the recess extends along the dental arch or dental arch section.

5. The denture base blank according to claim 1, wherein on at least one side of the denture base blank, a holder is arranged for affixing the denture base blank to a CAM device and/or a mark is provided for the positioning of the denture base blank.

6. The denture base blank according to claim 1, wherein the denture base blank comprises solely rounded corners and edges.

7. The denture base blank according to claim 1, wherein in the interior of the dental arch or dental arch section of the denture base blank and along the dental arch or dental arch section, a stiffening and/or a reinforcement of the material of the denture base blank is or are provided.

8. The denture base blank according to claim 1, wherein the dental arch is designed as a parabolic thickening of the material on an edge side of the denture base blank, or the dental arch section is designed as a thickening of the material on the edge in the form of a partial piece of a parabolic form of the denture base blank.

9. The denture base blank according to claim 8, wherein the thickening has a width between 8 mm and 30 mm and/or the thickening has a thickness between 5 mm and 30 mm.

10. The denture base blank according to claim 8, wherein the thickening has a greater thickness in an area around an apex of the parabolic thickening than in arms of the parabolic thickening and/or that the thickness of the thickening increases in a direction of the apex of the parabolic section.

11. A method for producing a denture base for the production of a total denture or at least a partial denture with a denture base blank according to claim 1, comprising the following method steps:
(a) affixing the denture base blank in a CAM device for the removal of material of the denture base blank using a CAM method, and
(b) removing material from the denture base blank with the CAM device on the basis of a calculated CAD model and creating several recesses for holding prosthetic teeth with the CAM method in the pre-formed dental arch of the denture base blank in the denture base produced.

12. The method according to claim 11, wherein the denture base blank is selected from a plurality of denture base blanks, wherein the selection is made using a calculation based on the CAD model of the denture base to be produced and the known dimensions of all denture base.

13. The method according to claim 12, wherein the denture base blank is selected or the denture base blanks are selected from the quantity of denture base blanks, outer dimensions of which can fully hold the form of the denture base to be produced, which is calculated by the CAD model.

14. The method according to claim 11, wherein when calculating the CAD model of the denture base to be produced, data previously recorded relating to an oral cavity situation of the patient and/or the outer form of the denture base blanks or the outer form of the denture base blank are taken into account.

15. A set comprising at least one denture base blank according to claim 1, and data regarding the outer form of the at least one denture base blank.

16. A set according to claim 15, wherein the set comprises several differently formed denture base blanks and data regarding the outer form of all these denture base blanks.

17. The denture base blank according to claim 5, wherein the CAM device is a CAM milling machine.

18. The denture base blank according to claim 1, wherein on at least a buccal side of the denture base blank, a holder is arranged for affixing the denture base blank to a CAM device and/or a mark is provided for the positioning of the denture base blank.

19. The denture base blank according to claim 18, wherein the CAM device is a CAM milling machine.

20. The denture base blank according to claim 6, wherein no corner or edge of the denture base blank has a curvature radius of less than 0.5 mm.

21. The denture base blank according to claim 20, wherein no corner or edge of the denture base blank has a curvature radius of less than 2 mm.

22. The method according to claim 12, wherein, by means of an output facility of a computer, all denture base blanks from the selection can be recommended and/or can be selected via an input facility.

23. The method according to claim 13, wherein the recommended sequence of the selected denture base blanks is determined by a volume difference between the outer form of the denture base blanks and the CAD model of the denture base to be produced.

24. The method according to claim 23, wherein the displayed or shown sequence of the selected denture base blanks is determined by a volume difference between the outer form of the denture base blanks and the CAD model of the denture base to be produced.

25. The method according to claim 11, comprising milling several recesses for holding prosthetic teeth with the CAM method in the pre-formed dental arch of the denture base blank in the denture base produced.

26. A set according to claim 15, comprising a plurality of differently formed denture base blanks.

27. A set according to claim 15, comprising a data carrier on which the data are stored.

* * * * *